(12) United States Patent
Dubner

(10) Patent No.: US 6,609,314 B1
(45) Date of Patent: Aug. 26, 2003

(54) MECHANICAL INTERIOR SHOE ADJUSTMENT

(76) Inventor: Benjamin B. Dubner, 84 Marcus Ave., New Hyde Park, NY (US) 11040

( * ) Notice: Subject to any disclaimer, the term of this patent is extended or adjusted under 35 U.S.C. 154(b) by 0 days.

(21) Appl. No.: 09/525,975

(22) Filed: Mar. 15, 2000

(51) Int. Cl.[7] ............................... A43B 7/14; A61F 5/14
(52) U.S. Cl. ............................. 36/156; 36/88; 36/93; 36/155; 36/150; 36/160
(58) Field of Search .................... 36/91, 88, 93, 36/34 R, 39, 82, 145, 149, 150, 151, 152, 155, 156, 157, 158, 160, 166, 168, 171, 173, 175, 177, 179, 180, 182

(56) References Cited

U.S. PATENT DOCUMENTS

| | | | | |
|---|---|---|---|---|
| 1,091,696 A | * | 3/1914 | Normandin | 36/156 |
| 1,558,192 A | * | 10/1925 | Lindgreen | 36/156 |
| 1,853,550 A | * | 4/1932 | Copithorn | 36/157 |
| 1,890,382 A | * | 12/1932 | Howell | 36/157 |
| 1,890,383 A | * | 12/1932 | Howell | 36/157 |
| 1,890,384 A | * | 12/1932 | Howell | 36/157 |
| 1,904,790 A | * | 4/1933 | Howell | 36/156 |
| 1,948,638 A | * | 2/1934 | Young | 36/156 |
| 2,012,311 A | * | 8/1935 | Howell | 36/156 |
| 2,114,089 A | * | 4/1938 | Trick et al. | 36/156 |
| 2,207,271 A | * | 7/1940 | Sheridan | 36/157 |
| 4,166,329 A | * | 9/1979 | Herbig | 36/91 |
| 5,285,584 A | * | 2/1994 | Dubner | 36/88 |

* cited by examiner

*Primary Examiner*—Anthony Stashick
(74) *Attorney, Agent, or Firm*—Murray Schaffer

(57) ABSTRACT

In a shoe, an apparatus for the support of a foot, comprising a semi rigid piece of metal or plastic extending from the heel to the ball of the foot, disposed over the inner sole of the shoe, and a screw penetrating upward to raise or lower the semi rigid piece.

2 Claims, 2 Drawing Sheets

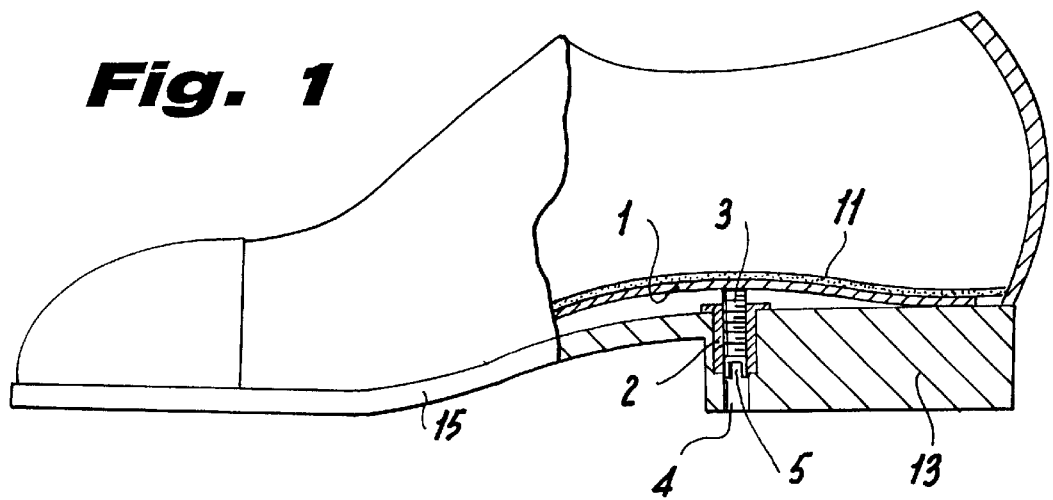
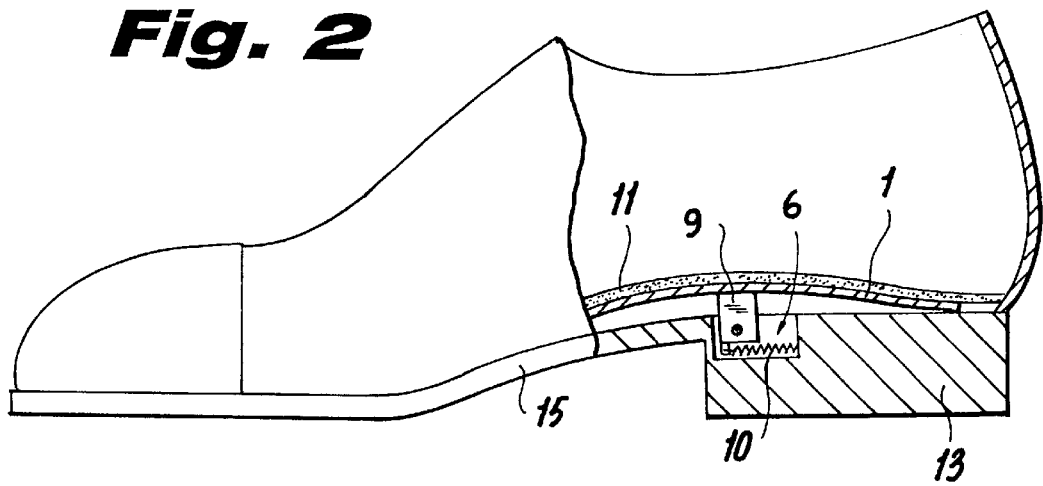
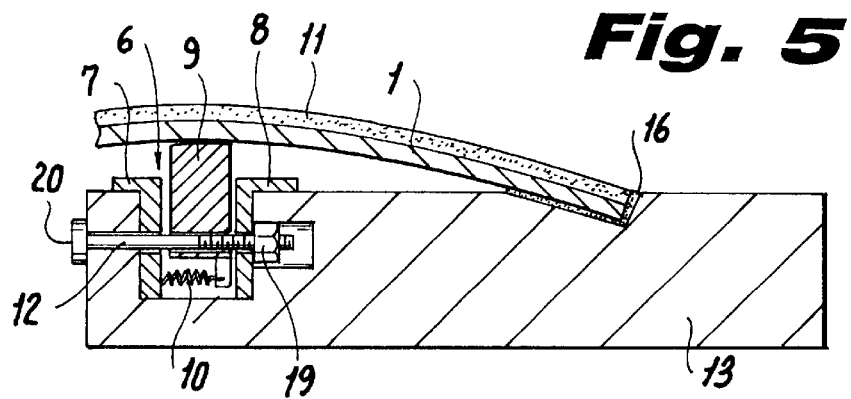

MECHANICAL INTERIOR SHOE ADJUSTMENT

BACKGROUND OF THE INVENTION

The invention relates generally to the field of footgear: dress shoes, athletic boots, sneakers, orthopedic shoes and the like, and more particularly to an improved means for quick, easy, inexpensive and therapeutic individual custom fitting by mechanical means within said footgear.

Walking is a complicated bio-mechanical process. As the heel strikes, the Talus and attached Calcaneous (heel) bone, which make up the Sub Taler joint, move downwardly and medially, acting as a shock absorber. The range of said movement is called pronation. The degree of pronation is a direct factor that determines the efficiency of the foot and leg as well as all related parts of the body above the foot, as well as the parts of the foot distal to these bones.

Abnormal degrees of pronation can cause incorrect positioning of all the directly and indirectly connected bones which in turn causes strain on all the directly and indirectly connected joints, ligaments, nerves, blood vessels and muscles. This strain may be felt any where throughout the body as aches, pains, fatigue, cramping, pulled muscles, fasciitis, tendenitis, etc. If left untreated the condition may worsen and cause chronic "bad knees", "bad backs", neuromas, stress fractures of bones, etc.

The degrees of pronation are also influenced by the kind of footgear and the fit of said footgear.

PRIOR ART

The problems arising from excessive pronation have been treated by devices worn in footgear to minimize the degree of pronation. Such "supports" are lumped together as "Arch Supports" and "Foot Orthotics". "Arch Supports" are relatively inexpensive- twenty, thirty dollars- and are sold over the counter, usually by shoe size. "Foot Orthotics" are custom built over plaster casts- or the like- of the individual foot and may cost four and five hundred dollars. The devices may be constructed and formed of leather, metals and plastics of varying degrees of rigidity. While the main benefits of such "supports" derive from the support under the Sub Taler joint, the "supports" mimic the shape of the bottom of the foot and often have built up edges to maintain the foot in position relative to the Sub Taler supported area.

All such devices have many faults in common. They take up space within the footgear. Their fit and efficiency is effected by the shape of the sole of the footgear. As they are constantly worn they pick up odors from the feet. The breakdown of the shoe with wear will change the efficiency of the devices. The condition of the person wearing said devices may change. Changing shoes, the wearer may forget to include the devices. They may be lost. Because of their cost a person may choose not to buy them and so allow his condition to worsen. A less expensive device may not be correct for the condition treated.

Adjustments of said devices are costly. It requires the services of persons trained in the art, who have the necessary machinery and materials. Adjustments also require the investment of travel time to and from the business or offices of the adjuster for one or more times.

It is therefore among the objects of the present invention to provide means for adjusting the interior of footgear to meet the needs of the individual foot, in which the advantages of the above are substantially retained, and the disadvantages substantially eliminated.

Another object of the invention lies in the provision of mechanical means to achieve the initial custom support, as well as subsequent adjustments, quickly, easily and inexpensively. Another object is to provide means by which an individual can adjust the shoe himself when necessary. The relatively small cost and ease of use may attract its use for even small problems and thus, in the long run, prevent many of the complications arising from neglect of treating small problems.

U.S. Pat. No. 5,285,584 granted to this inventor uses a similar screw means to raise the inner aspect of the heel. The devices of this Patent consists of two distinct parts. One part controls the Sub Taler joint (heel) area of the foot. The other part controls the forward ball of the foot (metatarsal) area. However, it has been found that the raising of the small area under the Sub Taler joint area puts a painful and unwearable pressure on that small area. A semi rigid extension extending under most of medial side of the foot can distribute this excessive pressure and make it bearable and wearable. However, such a semi rigid extension cannot be used with the aforementioned patent because such an extension would then extend over and impinge the mechanism for controlling the forward metatarsal area and interfere with the working of that part of the invention. Ref lexly, it would also interfere with the working of the Sub Taler (heel) part of that invention.

It is an object of the present invention to overcome the foregoing problem.

These objects and advantages will be apparent in the drawings.

SUMMARY OF THE INVENTION

In accordance with the present invention, a semi rigid piece along the long arch area, extends from the heel area to the ball of the foot area and is disposed over the inner sole of the shoe. This semi rigid piece may be of steel or plastic. The foot is maintained in position by the sides of the shoes.

The device is provided with lifting means to raise or lower the semi rigid piece. In the preferred embodiment, the lifting means is a screw that penetrates the shoe upwardly through the sole.

In another embodiment, a rigid supportive piece raises from a slit in the sole of the shoe in the Sub Taler joint heel area. This supportive piece is activated by a spring that causes it to revolve into a vertical position or as close to a vertical as the overriding semi rigid piece pressed against the foot will allow. A screw, penetrating from the side of the heel area goes through a bore in said supportive piece and acts as its axle. Tightening of this screw forces the supportive piece tightly against side flanged attachments to the wall of the slot to maintain its position.

BRIEF DESCRIPTION OF DRAWINGS

FIG. 1. is a longitudinal section of a shoe illustrating the semi rigid piece and the underlying screw mechanism penetrating up through the sole/heel;

FIG. 2. is a longitudinal section of a shoe illustrating another embodiment of an underlying mechanism with a controlling screw penetrating the side of the heel;

FIG. 5. is a sectional view taken along line A—A of FIG. 4, illustrating another means of raising and lowering the semi rigid piece controlled by a screw penetrating the side of the heel.

DESCRIPTION OF THE PREFERRED EMBODIMENTS

Figure 3:
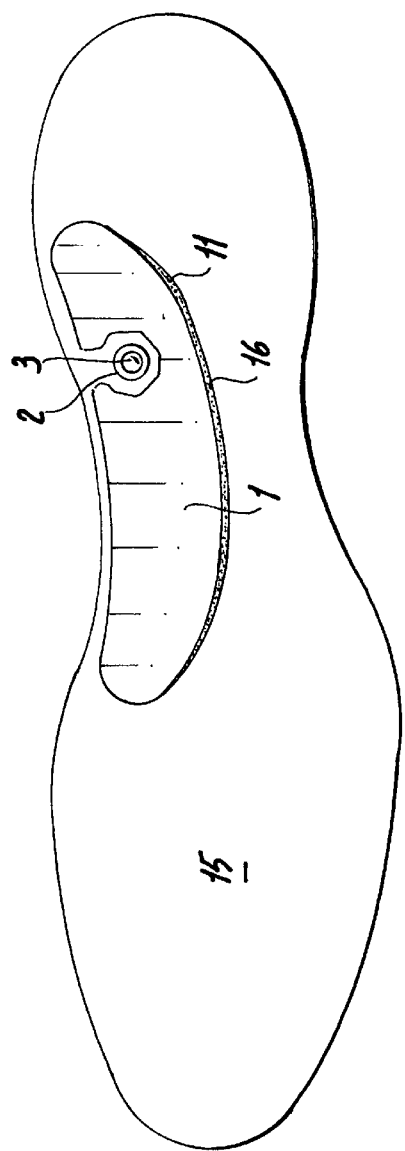
FIG. 3. is a plan view of the shoe sole shown in FIG. 1 illustrating the through bore of the heel.

The present invention fits conventional shoes made for men or women. Such shoes generally comprise a upper, a outer sole, a heel, a internal sole and a sock lining.

The invention, as seen in FIG. 1, provides a semi rigid piece 1, for supporting the arch of the foot, and an underlying flanged Tee Nut 2 set into the top of through bore 4 of the heel 13. Said Tee Nut 2 contains inner threads to mesh with the threads of screw 3. Screw 3 penetrates the bore 4 of the heel and contacts the bottom of the semi rigid piece 1 in the area of its heel end. Screw 3 has a notch 5 at its lower end to facilitate the use a screw driver to turn said screw 3 to raise or lower said semi rigid piece 1. The sock lining 11 is of a material that helps dissipate the pressure of the semi rigid piece 1. The semi rigid piece 1 is secured to the sock lining 11 directly by the use of adhesives or adhesive tapes.

With the foot in the footgear, the screw 3 is turned until the wearer feels the semi rigid piece 1 contact the medial area of the foot. Then, walking determines if the amount of raise is comfortable. If the wearer of the shoe is seeking relief from some particular pain or ache, some days or weeks trials are indicated. If there is no relief, piece 1 can be raised for other trials. If other areas of discomfort appear, the semi rigid piece 1 can then be lowered back to its comfortable position.

Figure 4:
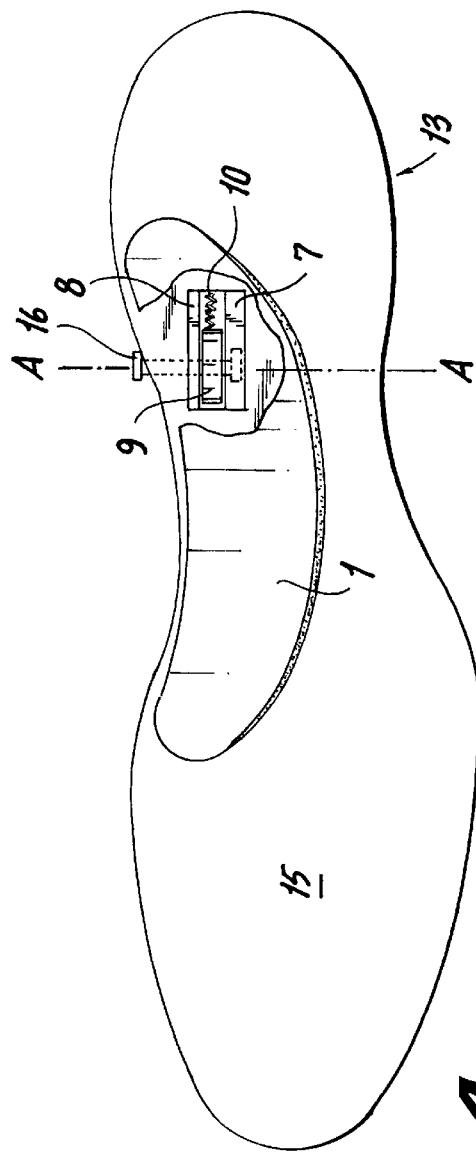
FIG. 4. is a plan view of a shoe sole illustrating yet another means of raising and lowering the semi rigid piece controlled by a screw penetrating the side of the heel.

In another embodiment of the invention as shown in FIGS. 2–4, said semi rigid piece 1 overlies a slot 6 in the sole area 15 of the heel 13. The slot 6 contains a supporting piece 9 and flanged pieces 7 and 8 attached to opposing walls of said slot 6 (FIG. 4). Operation of handle 16 provides counter clockwise rotation of screw 12 at the side of the heel 13 releasing the friction pressure holding said supporting piece 9 in place between flanged pieces 7 and 8. This frees piece 9 so it can respond to the urging of spring 10 and rotate up to and force up semi rigid piece 1 as much as it can until it is stopped by the pressure of the foot above it. Then screw 12 is turned via handle 16 clockwise within its nut 14 to bring said support piece 9 and the flanged pieces 7 and 8 tightly together to maintain support piece 9 and semi rigid piece 1 in position. Flanged pieces 7 and 8 are adhered to the walls of slot 6 by their flange parts. The sides of support piece 9 and the flange pieces 7 and 8 are roughened to provide additional friction to maintain support piece 9 in position.

In another embodiment of the invention as shown in FIGS. 2–5, the semi rigid piece 1 overlies a slot 6 in the sole area 15 of the heel 13. The slot 6 contains a supporting piece 9 and flanged pieces 7 and 8 attached to opposing walls of said slot 6 (FIG. 4). Operation of handle 16 provides counter clockwise rotation of screw 12 at the side of the heel 13 releasing the friction pressure holding said supporting piece 9 in place between flanged pieces 7 and 8. This frees piece 9 so it can respond to the urging of spring 10 and rotate up to and force up semi rigid piece 1 as much as it can until it is stopped by the pressure of the foot above it. Then screw 12 is turned via handle 16 clockwise within its nut 14 to bring said support piece 9 and the flanged pieces 7 and 8 tightly together to maintain support piece 9 and semi rigid piece 1 in position. Flanged pieces 7 and 8 are adhered to the walls of slot 6 by their flange parts. The sides of support piece 9 and the flange pieces 7 and 8 are roughened to provide additional friction to maintain piece 9 in position.

The semi rigid piece 1 forming the foot support can be made from a single member of flexible plastic or several layers or leaves of plastic, leather or the like.

With the foregoing and other objects in view, the invention resides in the novel arrangement and combination of parts and in the details of construction hereinafter described and claimed, it being understood that changes in the precise embodiments of the invention herein disclosed may be within the scope of what is claimed without departing from the spirit of the invention.

What is claimed is:

1. Apparatus for supporting a foot within a shoe, wherein the shoe has an inner sole and a long arch, said apparatus comprising a semi rigid piece disposed over the inner sole along the long arch area, means operative to variably raise and lower said semi rigid piece and maintain said semi rigid piece at a selected elevated position, said operative means comprising a support centrally disposed between two flanged side pieces secured within said sole and includes a screw penetrating said two flanged side pieces and support where tightening of said screw unites said support and said flanged side pieces in unmovable union.

2. The apparatus according to claim 1, wherein said support and said flange pieces are formed with cooperating teeth engageable on tightening of said screw to fix said support in selected position.

* * * * *